US008814858B2

(12) United States Patent
Rioux et al.

(10) Patent No.: US 8,814,858 B2
(45) Date of Patent: *Aug. 26, 2014

(54) METHOD FOR ABLATING TISSUE TO FACILITATE IMPLANTATION AND APPARATUS AND KIT FOR USE THEREWITH

(71) Applicant: Boston Scientific Scimed, Inc., Maple Grove, MN (US)

(72) Inventors: Robert F. Rioux, Ashland, MA (US); Paul DiCarlo, Middleboro, MA (US); Joseph Levendusky, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/688,560

(22) Filed: Nov. 29, 2012

(65) Prior Publication Data

US 2013/0090653 A1  Apr. 11, 2013

Related U.S. Application Data

(63) Continuation of application No. 12/171,223, filed on Jul. 10, 2008.

(60) Provisional application No. 60/959,441, filed on Jul. 13, 2007.

(51) Int. Cl.
| *A61B 18/14* | (2006.01) |
| *A61B 17/32* | (2006.01) |
| *A61C 19/06* | (2006.01) |
| *A61B 18/08* | (2006.01) |
| *A61F 5/00* | (2006.01) |
| *A61C 7/08* | (2006.01) |
| *A61C 9/00* | (2006.01) |

(52) U.S. Cl.
CPC ............... *A61B 18/082* (2013.01); *A61B 17/32* (2013.01); *A61C 19/06* (2013.01); *A61F 5/0069* (2013.01); *A61C 7/08* (2013.01); *A61C 9/0006* (2013.01)
USPC ............................................. 606/41; 606/190

(58) Field of Classification Search
CPC .... A61B 18/12; A61B 18/14; A61B 18/1492; A61B 2018/00011; A61B 2018/00029; A61B 2018/00065; A61B 2018/00077; A61B 2018/00238; A61B 2018/00577; A61B 2018/1472; A61F 5/0013
USPC ..................... 606/32, 37, 39–41, 46, 47, 190; 600/116; 607/98, 99, 115; 604/19, 21, 604/27, 28, 48, 514
See application file for complete search history.

(56) References Cited

U.S. PATENT DOCUMENTS

| 6,258,087 B1 * | 7/2001 | Edwards et al. ................ 606/41 |
| 2005/0288566 A1 * | 12/2005 | Levendusky et al. ......... 600/372 |
| 2006/0259027 A1 * | 11/2006 | Kwan et al. ..................... 606/41 |
| 2009/0177192 A1 * | 7/2009 | Rioux et al. .................... 606/33 |

FOREIGN PATENT DOCUMENTS

WO  WO 02/058577 A1 *  8/2002  ............. A61B 18/08

* cited by examiner

*Primary Examiner* — Michael Peffley
*Assistant Examiner* — Thomas Giuliani
(74) *Attorney, Agent, or Firm* — Fay Kaplun & Marcin, LLP (57) ABSTRACT

A method for treating a mammalian body having tissue comprising creating a cavity in the tissue formed by an internal surface of the tissue. The internal surface is ablated. An implant-forming material is introduced into the cavity to create an implant in the tissue. The ablation of the internal surface inhibits migration of the implant. An apparatus and kit for use with the method are provided.

10 Claims, 6 Drawing Sheets

METHOD FOR ABLATING TISSUE TO FACILITATE IMPLANTATION AND APPARATUS AND KIT FOR USE THEREWITH

PRIORITY CLAIM

The present application is a Continuation of U.S. patent application Ser. No. 12/171,223 filed on Jul. 10, 2008 which claims priority of U.S. Prov. Patent Application Ser. No. 60/959,441 filed on Jul. 13, 2007. The entire disclosure of these patents/applications is expressly incorporated herein by reference.

SCOPE OF THE INVENTION

The present invention relates to methods and devices for treating a mammalian body and more particularly to methods and devices for creating implants in tissue of a mammalian body.

BACKGROUND

Medical devices have been provided for the delivery of a material to various portions of a wall forming a vessel such as the gastrointestinal tract of a mammalian body to create implants in the wall. See, for example, U.S. Pat. No. 6,251,063. There remains, however, a need for inhibiting migration of such implants in the wall.

SUMMARY OF THE INVENTION

A method for treating a mammalian body having tissue comprising creating a cavity in the tissue formed by an internal surface of the tissue is provided. The internal surface is ablated. An implant-forming material is introduced into the cavity to create an implant in the tissue. The ablation of the internal surface inhibits migration of the implant. An apparatus and kit for use with the method are provided.

BRIEF DESCRIPTION OF THE DRAWINGS

The accompanying drawings, which are somewhat schematic in some instances and are incorporated in and form a part of this specification, illustrate several embodiments of the invention and, together with the description, serve to explain the principles of the invention.

DESCRIPTION OF THE INVENTION

Figure 1:
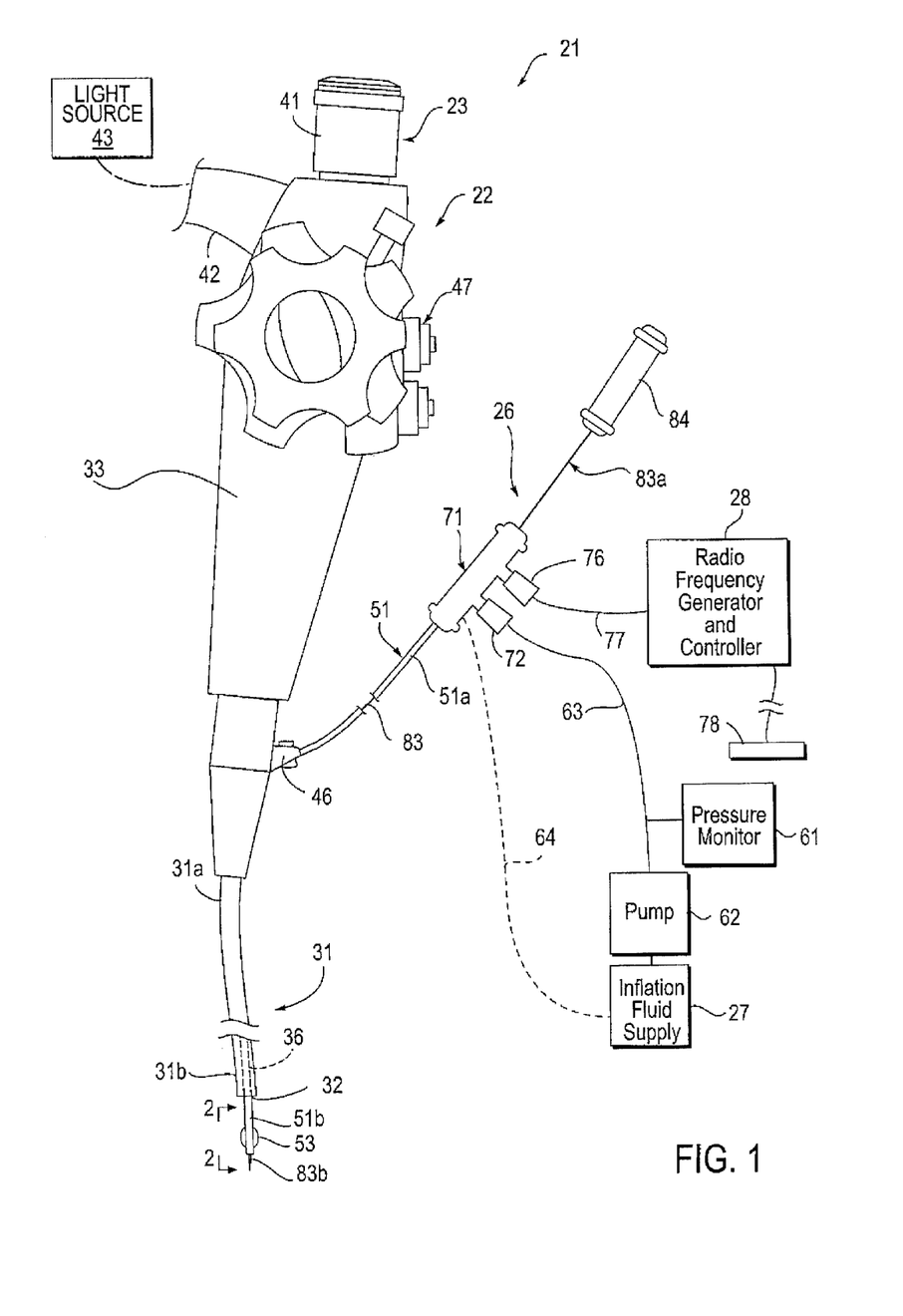
FIG. 1 is a plan view of a medical device having an apparatus for ablating tissue of the present invention for use in the method of the present invention.
Figure 3:
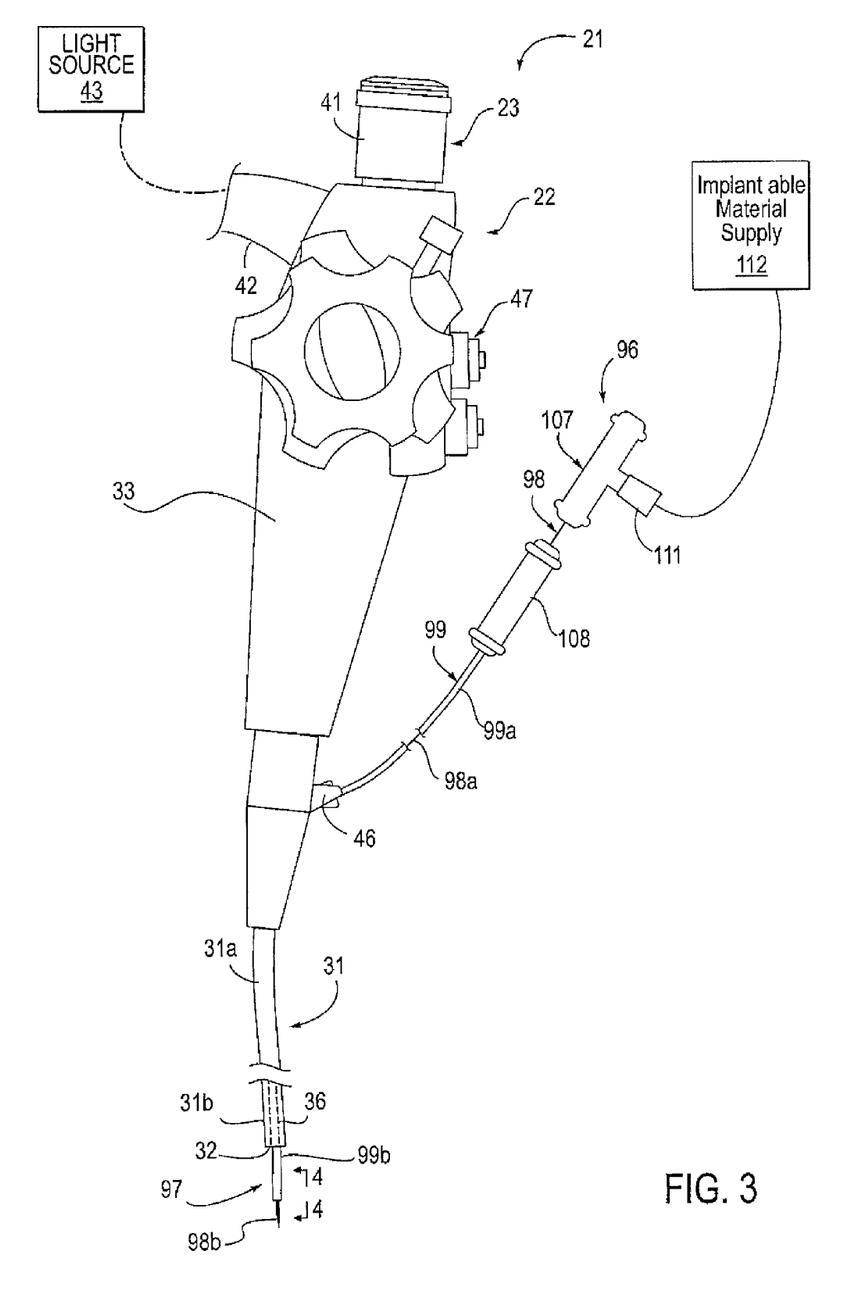
FIG. 3 is a plan view of the medical device of FIG. 1 having an implant-forming apparatus for use in the method of the present invention.

The method of the present invention can be performed with an apparatus or medical device of the type shown in FIGS. 1 and 3. The medical device 21 of FIG. 1 includes a probe member or probe 22 having an optical viewing device 23. A cavity-forming assembly or ablation apparatus 26 is slidably carried by probe 22. Treatment device 21 further includes an inflation fluid supply 27 coupled to the cavity-forming or ablation apparatus 26 and a radio frequency supply and controller 28 electrically coupled to the ablation apparatus 26.

A conventional or other suitable gastroscope or endoscope can be used for probe or catheter 22. An exemplary probe 22 includes a flexible elongate tubular member or insertion tube 31 having proximal and distal extremities 31a and 31b and a distal face 32. Insertion tube 31 has been sectioned in FIG. 1 so that only a portion of proximal extremity 31a and distal extremity 31b are shown. A handle means or assembly is coupled to proximal extremity 31a of the insertion tube 31 and includes a conventional handle 33. The tubular insertion tube 31 is provided with at least one bore and preferably a plurality of bores or passageways 36 extending from proximal extremity 31a to distal extremity 31b. A portion of one such passageway 36 is shown in dashed lines in FIG. 1.

Optical viewing device 23 is formed integral with probe 22 and has an optical element or objective lens (not shown) carried by one of the passageways 36 of the device 23. The objective lens has a field of view at distal face 32 which permits the operator to view forwardly of insertion tube distal extremity 31b. Optical viewing device 23 further includes an eye piece 41 mounted on the proximal end of handle 33. A connection cable 42, a portion of which is shown in FIG. 1, extends from handle 33 to a conventional light source 43. At least one light guide extends through cable 42 and insertion tube 31 for providing illumination forwardly of distal face 32 of the insertion tube 31.

One of the passageways 36 provided in insertion tube 31 extends to a side port 46 formed in handle 33. Ablation apparatus 26 can be slidably introduced into such passageway 36 by means of side port 46. Insertion tube 31 is flexible so as to facilitate its insertion and advancement through a body and is provided with a bendable distal end for selectively directing distal face 32 in a desired direction. A plurality of finger operable controls 47 are provided on handle 33 for, among other things, operating the bendable distal end of insertion tube 31 and the supply and removal of fluids through the insertion tube 31.

Figure 2:
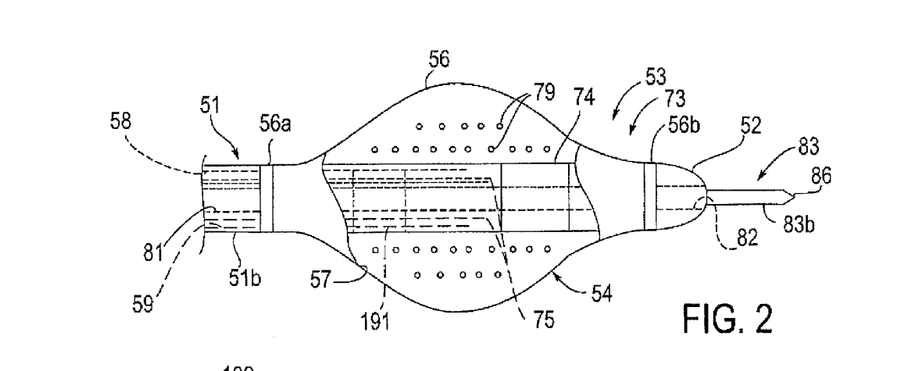
FIG. 2 is a side view, partially cut away, of the distal extremity of the apparatus for ablating tissue of FIG. 1 taken along the line 2-2 of FIG. 1.

Ablation apparatus 26 includes an elongate member 51 made from any suitable material such as plastic and more specifically a thermoplastic such as but not limited to polypropylene, polyethylene or nylon and more preferably polypropylene. The elongate member 51 has a proximal end portion or extremity 51a and a distal end portion or extremity 51b (see FIGS. 1 and 2). The elongate member preferably has a rounded end 52 at the distal extremity, as shown in FIG. 2, for facilitating blunt dissection of tissue. The ablation apparatus 26 further includes a tissue-dissecting or cavity-forming device 53 disposed on the distal extremity of the elongate member. Such device 53, also referred to herein as an inflatable device, preferably includes a balloon 54 and more preferably a perforated or "weeping" balloon, such as of the type described in U.S. Pat. No. 6,673,290, the entire content of which is incorporated herein by this reference. Balloon or dissecting element 54 has an expandable-collapsible body 56 made from any suitable material such as thermoplastic or any of the materials such as polyurethane disclosed in the table set forth below taken from Table 6 of U.S. Pat. No. 6,475,213, the entire content of which is incorporated herein by this reference.

annular spaced provided between the balloon body 56 and the elongate member 51. Balloon 54, that is the expandable portion of the balloon, has a length ranging from one to twenty millimeters and preferably ten millimeters and a width ranging from one to thirty millimeters and preferably five millimeters. The ablation apparatus 26 has a length so that when balloon 54 extends distally beyond face 32 of the insertion tube 31, proximal extremity 51a of the elongate member 51 is accessible at side port 46.

The elongate member 51 has at least a first lumen 58, and preferably a second lumen 59, extending longitudinally from the proximal extremity 51a to the distal extremity 51b of the elongate member (see FIG. 2). The first and second lumens 58 and 59 each opens into the hollow interior 57 of the expandable-collapsible body 56 at the distal extremity of the elongate member and is fluidly coupled to the inflation fluid supply 27 connected to the proximal extremity of the elongate member. First lumen 58 serves as an inflation lumen, and optional second lumen 59 serves as a return lumen when circulation of fluid is desired through balloon 54. Although any suitable fluid may be provided within supply 27, a conductive fluid is preferred and a saline solution is more particularly preferred. A finger-grippable element 71 is coupled to the proximal extremity of the elongate member 51 and includes at least one suitable fitting 72 for coupling the first lumen 58 to fluid supply 27 so as to permit fluid communication between supply 27 and inflation lumen 58. An optional pressure monitor 61 and an optional pump 62 can be fluidly coupled to the inlet line 63 from supply 27 to fitting 72, as Summary of Porous Ablation Materials

| Mat'l | Mfgr. | HPhb | HPhl | Pore Size | Bubble Point Value | No Flow Impedance | Impedance w/ Flow | Mat'l Brkdwn | Lesion Depth |
|---|---|---|---|---|---|---|---|---|---|
| Dialysis Tubing | Spectrum | | X | .025 μm | High | 87 Ω | 87 Ω | No | 13.3 mm |
| Nylon Mesh | Spectrum | | X | 5 μm | Med | 68 Ω | 69 Ω | No | 9.9 mm |
| Stain-St Mesh | Spectrum | | | 30 μm | Low | 67 Ω | 67 Ω | No | 9.7 mm |
| Polycarb Film | Millipore | | X | 1.2 μm | High 14 psi | 78 Ω | 78 Ω | No | 11.6 mm |
| Polyethersulfone | Gelman | | X | 5 μm | Med 1-6 psi | 80 Ω | 80 Ω | No | 10.6 mm |
| Modified Acrylic copolymer | Gelman | X | | 10 μm | Med 1-6 psi | 68 Ω | 68 Ω | Yes | 9.9 mm |
| Modified Acrylic copolymer | Gelman | X | | 5 μm | High | >300 Ω | 70 Ω | Yes | 11.0 mm w/ flow |
| Modified Acrylic w/ Backing | Gelman | X | | 10 μm | High | >300 Ω | 61 Ω | Yes | 11.3 mm w/ flow |

The foregoing table demonstrates that pore sizes may be decreased using hydrophilic materials, thereby minimizing or stopping liquid perfusion through the porous material, while till enabling ionic transport through the membrane. Hydrophobic porous materials make possible the realization of high resistivity porous electrodes. On the other hand, hydrophilic porous materials make possible the realization of low resistivity porous electrodes.

Body 56 is preferably tubular in conformation and has annular proximal and distal end portions 56a, 56b which are adhered or otherwise secured to distal extremity 51b of the elongate member 51 in longitudinally spaced apart positions by any suitable means such as an adhesive (not shown). The balloon 54 has an hollow interior or space 57 consisting of the illustrated in FIG. 1, A second suitable fitting 72 can be provided on element 71 when optional return lumen 59 is included in ablation apparatus 26. A return or outlet line 64 from such fitting, not shown in FIG. 1, is shown schematically as a dashed line from finger-grippable element 71 in FIG. 1.

Ablation apparatus 26 further includes at least one ablation element 73 provided on the distal extremity 51b of the elongate member 51. The expandable-collapsible body 56 is partially cut away in FIG. 2 to reveal an annular electrode 74 disposed within the interior 57 of the balloon 54 which is part of the ablation element 73. The active electrode 74 is electrically coupled to the radio frequency supply or generator 28 by, for example, a conductive wire or lead 75 (shown as a dashed line in FIG. 2) extending from the active electrode through the elongate member 51 to a connector 76 provided on grippable element 71 at the proximal extremity 51a of the elongate member 51. An electrical cable 77 is removably securable to the connector 76 and extends from the connector 76 to the radio frequency generator 28 (shown schematically in FIG. 1). When ablation element 73 is utilized in a monopolar mode, an indifferent or return electrode 78 is electrically coupled to generator and controller 28 and utilized. The indifferent or return electrode 78 is shown schematically in FIG. 1 and can be in the form of a ground pad.

A plurality of apertures or pores 79, some of which are shown in FIG. 2, extend through body 56 in spaced-apart positions for permitting ionic transport between the hollow interior of the expandable-collapsible body 56 and the exterior of the balloon 54, more specifically flow of the conductive fluid within the balloon to the exterior of the balloon. Although the diameter and spacing of pores 79 can be as described in U.S. Pat. No. 6,475,213, it is preferred that the pores have a diameter ranging from 0.025 to 30 microns, preferably five to 50 microns and more preferably five to ten microns. The placement of the pores 79 and the size of the pores 79 determine the porosity of the body 56. The porosity represents the space on the body 56 that does not contain material, or is empty, or is composed of pores 79. Expressed as a percentage, porosity represents the percent volume of the body 56 that is not occupied by the body material. For materials having a porosity greater than about 10%, porosity P (in %) can be determined as follows:

$$P=100(1-\rho_b/\rho_m)$$

where $\rho_b$ is the density of the body 56 as determined by its weight and volume, and $\rho_m$ is the density of the material from which the body 56 is made. To derive porosity for materials having a porosity of less than about 10%, a scanning electron microscope can be used to obtain the number of pores and their average diameter. Porosity P (in %) is then derived as follows:

$$P=N\pi(d^2/4)$$

where N is the pore density and equals ($p_n$/a), $p_n$ is the number of pores in the body 56, a is the total porous area of the body 56 (in centimeters$^2$), π is the constant 3.1416..., and d is the average diameter of the pores (in centimeters). As such, weeping balloon 54 can be considered part of the ablation element 73 of apparatus 26.

Elongate member 51 of ablation apparatus 26 can optionally include an additional lumen 81 extending longitudinally from proximal extremity 51a to an opening 82 at distal extremity 51b of the elongate member 51 (see FIG. 2). A suitable tissue-incising element such as a guidewire 83 is slidably disposed in lumen or passageway 81, as illustrated in FIGS. 1 and 2. Guidewire 83 has a proximal extremity 83a accessible from the proximal extremity 51a of the elongate member, and having a grip 84 secured thereto for facilitating hand-operable slidable movement of the guidewire 83 within passageway 81, and a distal extremity 83b with a sharpened or beveled tip 86 extendable from opening 82. The guidewire has a diameter ranging from 0.014 to 0.018 inch.

Treatment device 21 includes an implant-forming apparatus which, after removal of ablation apparatus 26 from passageway 36 and side port 46 of probe 22, can be introduced through the side port 46 into the passageway 36 as illustrated in FIG. 2. Such implant-forming apparatus can be in the form of a needle assembly or injection device 96 similar to that shown and described in U.S. Pat. No. 6,251,063, the entire content of which is incorporated herein by this reference. More specifically, injection device 96 includes a stylet 97 having a needle member 98 provided with a proximal end portion or extremity 98a and a distal end portion or extremity 98b and an optional sleeve member or sleeve 99 provided with a proximal end portion or extremity 99a and a distal end portion or extremity 99b (see FIGS. 2 and 4). Sleeve or first tubular member 99 is made from any suitable material such as flexible plastic or metal and has a lumen 102 extending longitudinally therethrough for receiving at least part of the needle member or second tubular member 98. Although the sleeve 99 and the needle member 98 can be fixed relative to each other, they are preferably slidable relative to each other in a longitudinal direction. In this regard, needle member 98 is slidably disposed in sleeve 99 and movable between a retracted position in which the needle member is recessed within distal end portion 99b of sleeve and an extended position in which the needle member 98 projects distally of the sleeve 99. Needle member 98 and sleeve 99 are slidably disposed within passageway 36 and side port 49 of insertion tube 31 and each have a length so that when distal end portions 98b and 99b are extending from distal extremity 31b of the insertion tube 31 or otherwise in the vicinity of distal face 32, proximal end portions 98a and 99a are accessible at side port 46.

Figure 4:
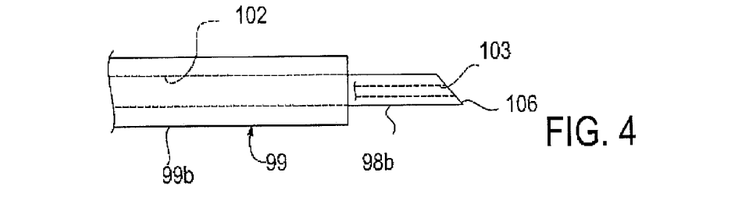
FIG. 4 is a side view, partially cut away, of the distal extremity of the implant-forming apparatus of FIG. 3 taken along the line 4-4 of FIG. 3.

The hollow or tubular needle member 98 has a lumen or passage 103 extending longitudinally therethrough from proximal end portion 98a to distal end portion 98b (see FIG. 4). In one preferred embodiment of injection device 26, the proximal end portion 98a of the needle member 98 and the central portion (not shown) of the needle member 98 are made from flexible plastic tubing and the distal extremity 98b of the needle member is a slender tube or needle 104 made from metal, rigid plastic or any other suitable material. Needle 104 is pressed into or otherwise suitably attached to the distal end of such flexible plastic tubing of the needle member 98. Metal needle 104 is preferably made from stainless steel and has a size ranging from 14 to 30 gauge, preferably ranging from 23 to 26 gauge and more preferably approximately 23 gauge. Where a 23 gauge needle 104 is provided, the internal diameter of needle bore or passage 103 can range from 0.012 to 0.017 inch. Needle 104, as shown in FIG. 4, is preferably provided with a sharpened or beveled distal tip 106.

A fluid connector 107 is secured or coupled to proximal end portion 98a of needle member 98 and a gripping member or grip 108 is secured to the proximal end portion 99a of the sleeve 99 (see FIG. 1). Fluid connector 107 includes at least one luer fitting portion 111, or any other suitable fitting portion, which communicates with the passageway 103 in needle 98. Supply or reservoir 112 is coupled to the proximal extremity of injection device 26, and preferably to the proximal extremity 98a of needle member 98, and can be of any suitable type. For example, one or more syringes for containing an implantable or injectable material of the present invention, or the ingredients thereof, can be included in supply 112. The supply 112 is included within the means of medical or treatment device 21 for introducing at least one liquid, solution, composition or material through passage 103 of needle 98 and out the at least one distal opening provided in the distal extremity 98b of needle member 98.

When needle member 98 and sleeve 99 are not fixed relative to each other, fluid connector 107 and grip 108 are movable longitudinally relative to each other so as to cause relative longitudinal movement between needle member 98 and sleeve 99. More specifically, grip 108 can be slid forwardly and rearwardly on proximal end portion 98a of the needle 98 relative to fluid connector 107. Movement of grip 108 forwardly relative to fluid connector 107 causes distal end portion 99b of sleeve 99 to extend fully over distal end portion 98b of the needle member 98 so that the needle 104 is fully recessed within sleeve 99. Conversely, movement of grip 108 rearwardly relative to fluid connector 107 causes sleeve distal end portion 99b to retract relative to needle distal end portion 98b so as to expose needle 104 distally of the sleeve 99.

Exemplary implantable materials or compositions which can be included in supply 112 and thus utilized in the method and apparatus of the present invention include any suitable material or composition from which an implant can be formed when a fluid, separately or in conjunction with another fluid, is introduced into the tissue of a body. The implant-forming material hereof includes solutions. Although aqueous or nonaqueous solutions are among the fluids that can be used, an inert, nonresorbable material is preferred. Preferred nonaqueous solutions are any of the solutions disclosed in International Application No. PCT/US99/29427 filed Dec. 10, 1999, the entire content of which is incorporated herein by this reference. One such injectable or implant-forming material comprises at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a solution which can be introduced into the body as a liquid and from which a solid thereafter precipitates or otherwise forms. A preferred embodiment of such a solution is a solution of a biocompatible composition and an optional biocompatible solvent which can further optionally include a contrast agent for facilitating visualization of the solution in the body. The solution can be aqueous or nonaqueous. Exemplary biocompatible compositions include biocompatible prepolymers and biocompatible polymers.

A particularly preferred implant forming solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 μm or less. It should be appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly(C1-C6) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly (C1-C6) acrylates, acrylate copolymers, polyalkyl alkacrylates wherein the alkyl and alk groups independently contain one to six carbon atoms, cellulose acetate butyrate; nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 μm or less. Other water insoluble contrast agents include gold, tungsten and platinum powders. Methods for preparing such water insoluble biocompatible contrast agents having an average particle size of about 10 μm or less are described below. Preferably, the contrast agent is water insoluble (i.e., has a water solubility of less than 0.01 mg/ml at 20° C.)

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the bio compatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the non-aqueous solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 μm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

When the prepolymer is liquid (as in the case of polyurethanes), the use of a biocompatible solvent is not absolutely necessary but may be preferred to provide for an appropriate viscosity in the nonaqueous solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Specific embodiments of nonaqueous solutions suitable for use in the apparatus and methods of the invention are described in U.S. Pat. Nos. 5,667,767 dated Sep. 16, 1997, 5,580,568 dated Dec. 3, 1996 and 5,695,480 dated Dec. 9, 1997 and International Publication Number WO 97/45131 having an International Publication Date of Dec. 4, 1997, the entire contents of which are incorporated herein by this reference.

Other suitable implantable materials include any material capable of being delivered through a needle, solutions, suspensions, slurries, biodegradable or nonbiodegradable materials and two part or other mixtures. Exemplary implantable materials include injectable bioglass as described in Walker et al., "Injectable Bioglass as a Potential Substitute for Injectable Polytetrafluorethylene Particles", 148:645-7, 1992, small particle species such as polytetrafluoroethylene (PTFE) particles in glycerine such as Polytef®, bio compatible compositions comprising discrete, polymeric and silicone rubber bodies such as described in U.S. Pat. Nos. 5,007,940, 5,158, 573 and 5,116,387 to Berg, biocompatible compositions comprising carbon coated beads such as disclosed in U.S. Pat. No. 5,451,406 to Lawin, collagen and other biodegradable material of the type disclosed in U.S. Pat. No. 4,803,075 to Wallace et al., biocompatible materials such as disclosed in U.S. Pat. No. 6,296,607 to Milbocker, U.S. Pat. No. 6,524, 327 to Spacek, and U.S. Publication Nos. 2002/0049363 and 2003/0135238 to Milbocker, and other known injectable materials.

Figure 5:
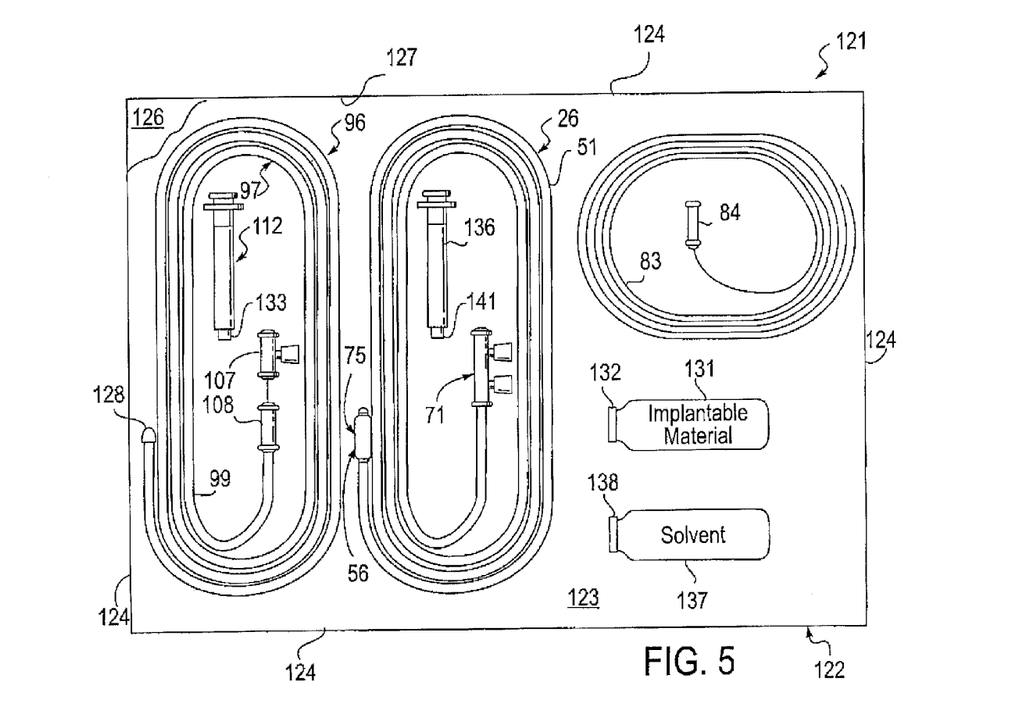
FIG. 5 is a plan view of a kit, somewhat schematic and partially cut away, for treating the upper portion of the gastrointestinal tract in accordance with the method of the present invention.
Figures 6, 7, 8:
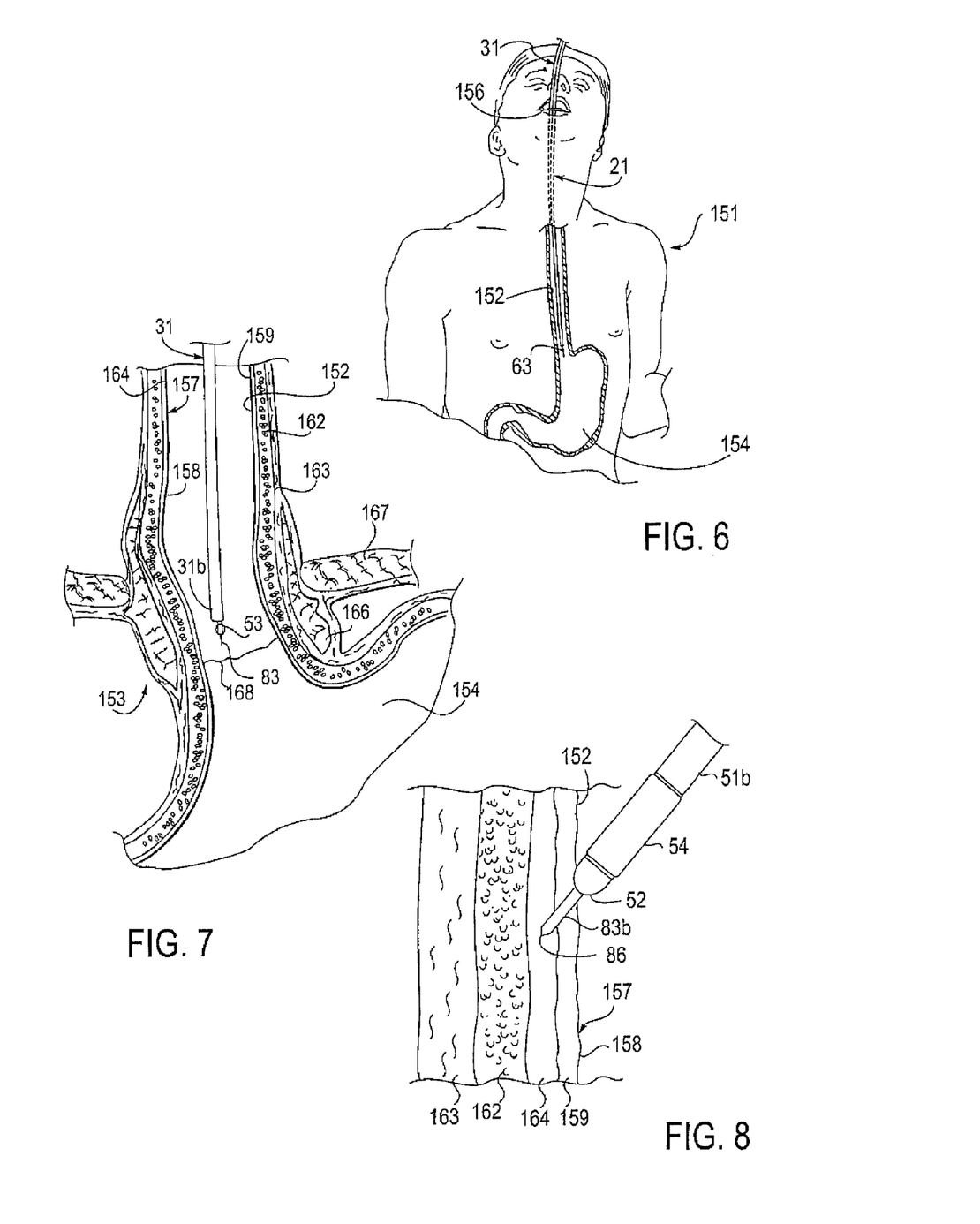
FIG. 6 is an elevational view of a portion of the medical device of FIG. 1 in a passageway of a mammalian body.
FIG. 7 is an enlarged view of a portion of the medical device of FIG. 1 in a passageway of a mammalian body.
FIG. 8 is an enlarged view of the distal extremity of the apparatus for ablating tissue of FIG. 1 penetrating tissue in a passageway of a mammalian body.

A kit 121 for a use in treating a wall forming the upper portion of a gastrointestinal tract in a human body in accordance with the method of the present invention is shown schematically in FIG. 5. Kit 121 includes a package 122 made from any suitable material such as cardboard or plastic for carrying the contents thereof. An exemplary package 122, shown in FIG. 5, is a box formed from a bottom wall 123, four side walls 124 and a top wall 126. A portion of top wall 126 is cut away in FIG. 5 to reveal an internal space 127 formed by walls 123, 124 and 126. The contents of receptacle or package 122 are disposed in internal space 127.

Ablation apparatus 26 is carried by package 122 within internal space 127. As discussed above, the ablation apparatus 26 includes elongate member 51 having an inflatable device 53 and an ablation element 73 on the distal extremity thereof. Kit 121 further includes injection device or needle assembly 96 carried by package 122 within internal space 127. The injection device 96 includes stylet 97 having needle member 98 and optional sleeve 99. A cap 128 is removably attached to distal end portion 99b of the sleeve 99 for protecting users against undesirable punctures by needle 104 during storage and setup.

A reservoir or syringe 112 and a container or vial 131 of the implantable material referred to above can optionally be included, separately or together, within kit 121. Where vial 131, shown with cap 132 in FIG. 5, contains a solution for example of an implant-forming material, luer fitting portion 133 of the syringe 112 is removably coupleable to cap 132 of the vial 131. The luer fitting portion 133 of the syringe 112 is also removably coupleable to fitting 72 of finger-grippable element 71 of injection device 96. Additional optional components of kit 121 include a second reservoir, such as syringe 136, and a container of a biocompatible solvent such as DMSO in the form of vial 137. Vial 137 includes a cap 138 and syringe 136 has a luer fitting portion 141 removably coupleable to cap 138 of the vial 137. Kit 121 can optionally further include a suitable incising element such as guidewire 83. A third reservoir or syringe (not shown) and/or a vial of aqueous solution such as saline solution (not shown) can also be optionally included in kit 121.

To assist in describing the utilization of the devices and practice of the method of the present invention, a portion of a mammalian body, in this case a human body 151, is shown in FIGS. 6-12. Body 151 has an internal cavity in the form of the passage of the esophagus 152 extending through a lower esophageal sphincter 153 to a stomach 154. Such cavity is accessible by a natural body opening in the form of mouth 156 and is defined by a wall 157 having a surface 158 which surrounds the esophagus. Esophagus 152 is part of the gastrointestinal tract of body 151 that extends from mouth 156 to an anus (not shown). The esophageal mucosa 159 serves as the inner layer of the intraluminal wall 157 in the esophagus 152. Wall 157 has a plurality of tissue layers, including a muscle layer comprising layer of circular muscle 162 extending beneath mucosa layer 159 and layer of longitudinal muscle 163 beneath circular muscle 162. The muscle layers 162 and 163 each extend around the esophagus 152 and the stomach 154. Wall 157 further includes a submucosal layer or submucosa 164 extending between mucosa 159 and muscle layers 162 and 163. A submucosal space, that is a potential space, can be created between submucosa 164 and circular muscle layer 162 by the separation of layer 159 from muscle layer 162. In addition, as with any muscle, wall 157 includes an intramuscular potential space, that is a space which can be created intramuscularly by distension and separation of muscle fibers within a single muscle, such as for example separation or dissection of circular muscle layer 162 from longitudinal muscle layer 163. Wall 157 has a depth or thickness which includes at least mucosal layer 159, submucosal layer 164, circular muscle layer 162 and longitudinal muscle layer 163. The phreno-esophageal ligament 166 and diaphragm 167 extend around the esophagus 152 above the lower esophageal sphincter 153. "In the vicinity of the lower esophageal sphincter," as that term is used herein, includes at least the lower third of the esophagus 152, the squamous columnar junction 168, and the gastric cardia or upper portion of the stomach 154.

Although medical device 21 can be used in any number of procedures, in one preferred procedure the device is introduced into a natural body opening to access a vessel in the body such as a passageway or an organ. In a further preferred procedure, device 21 can be utilized to deliver of a material, such as a fluid, solution or composition, to a wall of a passageway within a mammalian body to treat the body and more particularly to treat the wall forming the gastrointestinal tract of a mammalian body. Exemplary procedures can include the treatment of gastroesophageal reflux disease as described in part in U.S. Pat. Nos. 6,238,335 and 6,251,064, the treatment of the gastrointestinal tract and other cavities in a mammalian body as described in part in U.S. Pat. Nos. 6,251,063 and 6,575,896, the treatment of morbid obesity as described in part in U.S. Pat. Nos. 6,540,789, 6,802,863, 7,044,979 and 7,364,591 and the treatment of fecal incontinence as described in part in U.S. Pat. Nos. 6,533,717 and 6,595,910, the entire content of each of such patents being incorporated herein by this reference. In each of such procedures, an implant can be formed in a muscle or other layer of a wall forming an internal cavity of a mammalian body to reduce the distensibility of or otherwise treat the tissue of the wall, for example muscle in the wall in the vicinity of a sphincter. The exemplary procedure utilized for describing the devices and methods of the present invention is the treatment of gastroesophageal reflux disease.

In operation and use of medical device 21 having ablation apparatus 26 and injection device 96 in the method of the present invention, kit 121 is opened and the distal extremity 51b of elongate member 51 is inserted into side port 46 of probe 22 and slid through the probe passageway 36 so that the dissecting element 54 and ablation element 73 are carried by the distal extremity 51b of the elongate member 51. Balloon 54 and the rounded end 52 of elongate member 51 are preferably recessed within the passageway 36. Guidewire 83 is removed from kit 121 and wire distal extremity 83b is slid through finger-grippable element 71 into passageway 81 of the elongate member 51 so that the distal tip of the guidewire is disposed proximally of distal opening 82 of the passageway 81. In this manner, incising element 83 is carried by the distal extremity 51b of the elongate member 51. A suitable inflation fluid supply 27, such as a syringe or other suitable reservoir of a saline solution, is fluidly coupled to fitting 72 of finger-grippable element 71 by means of inlet line 63. Optional pressure monitor or gauge 61 and pump 62 can be included in line 63 between supply 27 and fitting 72. A radio frequency generator and controller 28 is electrically coupled to connector 77 of the element 73 and a return electrode 78 is electrically coupled to the generator 28. Probe 22 is prepared by connecting light cable 42 to light source 43 and attaching the proper eye piece 41 to handle 33. In addition, all other conventional attachments are applied to probe 22.

During the preparation of the patient, return electrode or ground pad 78 is adhered or otherwise affixed to the backside or another suitable exterior location on the patient. After the patient has been appropriately sedated or anesthetized, probe handle 33 is grasped by the physician to introduce distal extremity 31b of probe 22 into mouth 156 and advance insertion tube 31 down esophagus 152 to the vicinity of the lower esophageal sphincter 153. Insertion tube 31 has a length so that when distal extremity 31b is in the vicinity of the tissue being treating, in this case in the vicinity lower esophageal sphincter 103, proximal extremity 31a is outside of body 151.

Figure 9:
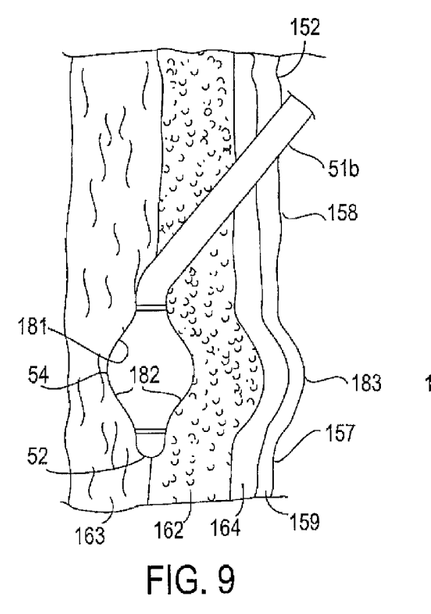
FIG. 9 is an enlarged view of the distal extremity of the apparatus for ablating tissue of FIG. 1 dissecting tissue in a passageway of a mammalian body.

Under the guidance of optical viewing device 23, the physician moves distal extremity 31b of the insertion tube 31 to the appropriate location near lower esophageal sphincter 153. Rounded end 52 of ablation apparatus 26 is then advanced distally from passageway 36 towards tissue wall 157 and then guidewire distal extremity 83b is advanced distally from opening 82 of the ablation apparatus towards the wall 157. In one preferred procedure, the outer surface 158 of wall 157 is cut or nicked by sharpened tip 86 of the guidewire 83 (see FIG. 8). Guidewire distal extremity 83b is then retracted into elongate member 51 of the ablation apparatus 26 and rounded end 52 of the ablation apparatus pushed through surface 158 into the incision or slit made by the guidewire by the physician grasping finger-grippable element 71 and moving it towards side port 46. Rounded end 52 can then be pushed deeper into wall 157 to extend the depth of the incision. The presence of guidewire 83 within passageway 81 of the ablation apparatus 26 desirably stiffens the apparatus 26 during such blunt dissection of wall 57. Upon reaching one of muscle layers 162 and 163, for example, the boundary between circular muscle layer 162 and longitudinal muscle layer 163, further advancement of distal extremity 51b of the ablation apparatus 26 causes a dissection or separation of the circular muscle layer 162 from the longitudinal muscle layer 163, as shown in FIG. 9. Although not required, it is preferred that distal extremity 51b of the ablation apparatus 26 be introduced a sufficient distance within wall 157 so that the entire length of balloon 54 extends between the layers of tissue which are intended to be separated, for example between circular muscle layer 162 and longitudinal muscle layer 163 as shown in FIG. 9, or alternatively between submucosal layer 164 and circular muscle layer 162.

It is appreciated that other methods may be utilized for introducing distal extremity 51b of the ablation apparatus 26 to a desired location within wall 157. For example, after guidewire 83 has been used as discussed above to initially incise tissue wall 157, the guidewire can be pushed distally further into wall 157 to a desired location, for example to a location which will permit the desired placement of balloon 54 within the wall 157. In another example, guidewire 83 may be utilized separately from ablation apparatus 26 and introduced into side port 46 and insertion tube passageway 36 without ablation apparatus 26. The sharpened tip 86 of the guidewire can thereafter penetrate wall 157 and distal extremity 83b of the guidewire advanced into the wall to a desired location, such as discussed above. After the guidewire 83 has penetrated wall 157 to a desired depth, the guidewire 83 then be withdrawn from probe 22 and ablation apparatus 26, without the guidewire 83 therein, inserted into passageway 36 of the probe. The operating physician thereafter pushes rounded end 52 of the ablation apparatus into the incision made by guidewire 83 until balloon 54 is at a desired location within such incision or, in a manner similar to that discussed above, is pushed further into the wall 157 so as to extend the length of the incision within the wall. In such a procedure, ablation apparatus 26 would not require optional passageway 81.

Where guidewire 83 is utilized for making an incision in wall 157, the penetration of the guidewire into wall can be monitored under direct visualization by means of optical viewing device 23 and the depth of penetration determined by any suitable means, for example by visualization through optical device 23 of gradations provided on distal extremity 83b of the guidewire or by visualization outside body 151 of the patient of gradations provided on proximal extremity 83a of the guidewire. In another approach, a depth stop can be placed on proximal extremity 83a of the guidewire for limiting distal travel of the guidewire. In yet another approach, the apparatus and process of monitoring depth by measuring impedance as disclosed in U.S. patent application Ser. No. 11/120,436 filed May 2, 2005, the entire content of which is incorporated herein by this reference, can be utilized.

Other devices can be used, separately or in combination with ablation apparatus 26, for creating an incision in wall 157 into which balloon 54 is disposed. For example, a radio frequency device with a sharpened-tip radio frequency electrode at the distal end thereof can be provided for creating an incision into which balloon 54 is introduced or rounded end 52 of the ablation apparatus 26 disposed for extending the length of the incision.

Once balloon 54 has been properly positioned within the wall 157, the physician inflates the balloon so as to further dissect tissue within wall 157 and thus create a cavity or pocket within the wall (see FIG. 9). In this regard, the fluid within inflation fluid supply 27 is introduced through inflation lumen 58 into balloon interior 57 so as to cause the balloon 54 to inflate. Pump 62 or hand pressure can be utilized for urging the inflation fluid into balloon 54. In FIG. 9, balloon 54 has been inflated between circular muscle layer 162 and longitudinal muscle layer 163 so as to create a cavity or pocket 181 formed by an internal surface 182 of muscle layers 162 and 163. The size of the inflated balloon 54, and hence the size of cavity 181, can be predetermined by introducing a known amount of inflation fluid into the balloon. In this manner, cavities of different size can be created by introducing appropriate predetermined volumes of inflation fluid into the balloon 54.

The location of cavity 181 within the tissue of wall 157 can be monitored by optical viewing device 23 to determine if the implant to be formed is at the proper longitudinal and latitudinal location within the esophagus 152 and within the muscle layer of wall 157. In this regard, the inflated balloon 54 causes a bulge 183 to form on the interior surface 158 of wall 157. The location of the bulge on wall 157 determines the longitudinal and latitudinal location of cavity 181 while a changed characteristic of surface 158 of the wall 157 at the bulge can indicate in which tissue layer of wall 157 the cavity 181 has been formed. For example, if surface 158 at the bulge 183 is not discolored, that is it remains the same color as the color of the adjacent portions of the wall 157, cavity 181 has been formed within the muscle layer of wall 157. If bulge 183 is discolored, for example under fluoroscopy the contrast is black or under ultrasound the cavity 181 is black or under optical the tissue forming the bulge turns from dark grey to dark red and then to brown, then cavity 181 has been formed in submucosa layer 164 or the mucosa 158 of the wall 157. As discussed above, it is preferred that cavity 181 be formed within one or both of muscle layers 162 and 163 and preferably between the layers 162 and 163 as shown in FIG. 9.

The location of cavity 181 within the tissue of wall 157, that is the layer of tissue in the wall in which the cavity is located, can additionally be determined by monitoring the pressure required to inflate balloon 54. Such pressure monitoring can be accomplished, for example, by means of pressure monitor 61 which periodically or continuously checks the pressure in inlet line 63 and thus the output of pump 62. In this regard, the pressure required to inflate balloon 54 between circular muscle layer 162 and longitudinal muscle layer 163 can be predetermined through empirical testing involving previous procedures or cadavers. In a similar manner, the pressures required to inflate balloon 54 at other depths and corresponding locations in wall 157 can be predetermined. The values read by monitor 61 can be compared by these predetermined values during the procedure so as to provide the physician with the location of cavity 181 within wall 157 and specifically within the plurality of tissue layers of the wall 157.

Figure 10:
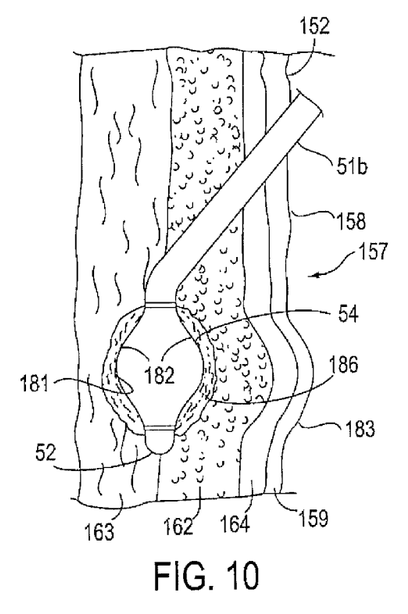
FIG. 10 is an enlarged view of the distal extremity of the apparatus for ablating tissue of FIG. 1 ablating tissue in a passageway of a mammalian body.
Figure 11:
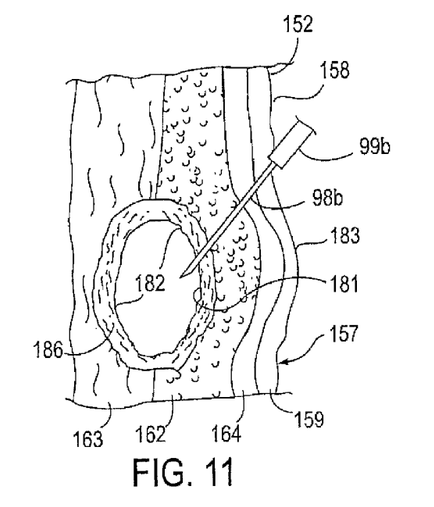
FIG. 11 is an enlarged view of the distal extremity of the implant-forming apparatus of FIG. 3 penetrating a cavity in tissue of a passageway of a mammalian body.
Figure 12:
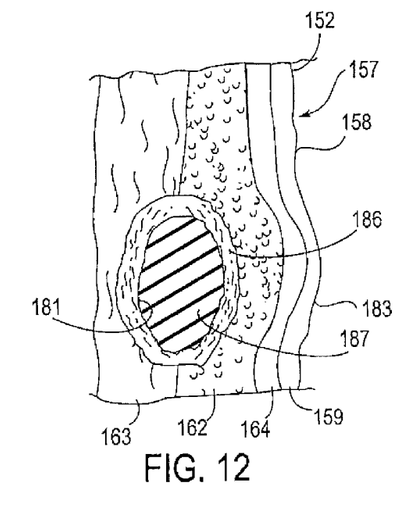
FIG. 12 is a cross-sectional view of an implant formed by the method of the present invention in tissue of a passageway of a mammalian.

Internal surfaces 182 of cavity 181 are thereafter ablated by the physician. In this regard, radio frequency energy provided by radio frequency generator and controller 28 is supplied to ablation apparatus 26, and specifically, to ablation element 73 provided on the distal extremity of the ablation apparatus. Electrode 74 is thus energized and radio frequency energy therefrom travels through the conductive inflation fluid within balloon 54 and travels with such fluid as it weeps out through pores 79 in the balloon. The radio frequency energy travels from balloon 54 to return electrode 78 in a conventional manner so as to ablate the tissue of the wall 157 in the vicinity of and more specifically surrounding the balloon 54. The amount of fluid seepage through pores 79 is generally very small and thus does not significantly affect the pressure required by pump 62 or other inflation device to inflate balloon 54. A layer of ablated tissue 186, also referred to herein as a lesion 186, so formed by ablation element 73 is shown in FIG. 10. The weeping fluid from balloon 54 serves to moisten the tissue surrounding the balloon and thus permit the ablation lesion to expand outward and form a deep lesion. In one preferred procedure, the amount of watts supplied by the generator 28 can be based on one or both of time and impedance feedback.

When it is desired to create a deeper lesion surrounding cavity 181, the inflation fluid can optionally be recirculated through inlet line 63 and inflation lumen 58 to interior 57 of the balloon 54 and back out of the balloon through return lumen 59 and return line 64. As the saline solution or other inflation fluid recirculates through inflation fluid supply 27, or any other conventional cooling mechanism, the solution or other fluid can be cooled so that a predetermined and desired fluid temperature is maintained within balloon 54 during the ablation process. Such cooled fluid serves to cool the tissue surrounding cavity 181 so as to prevent tissue necrosis and thereby increase the depth of the lesion created in the tissue adjacent the balloon 54 by ablation element 73.

Upon completion of the ablation process, balloon 54 is deflated and the ablation apparatus 26 removed from probe 22. The ablation of the internal surfaces 182 of cavity 181, and the resulting lesion 186 formed thereby, inhibits the collapse of cavity 181 upon the deflation and removal of balloon 54. In one embodiment, injection device 96 is inserted into the probe by introducing respective distal extremities 98b and 96b of the needle member 98 and sleeve 99 into side port 46 and passageway 36. Needle member 98 and sleeve 99 are each moveable between a first position in which distal extremities or end portions 98b and 99b are each retracted within insertion tube 31, and thus recessed within passageway 36 of the insertion tube, and a second position in which the distal end portions 98b and 99b extend distally beyond the distal end of insertion tube 31. The needle member 98 and sleeve 99 each have sufficient lengths so that the physician can extend them distally from the end of insertion tube 31a sufficient distance, should that be desired, by use of respective fluid connector 107 and grip 108. Supply 27 is filled with an appropriate material in preparation of the procedure and coupled to the proximal extremity of needle member 98 by means of fluid connector 107.

The physician causes the sharpened tip of needle 104 to penetrate wall 157 in the vicinity of bulge 183 and thereafter moves the needle member 98 distally a sufficient distance so that the distal end of the needle 104 enters cavity 181. The field of view of optical viewing device 23 facilitates observation of the penetration of wall 157 by needle member 98. The physician then causes an appropriate amount of the implantable or injectable material to be introduced through needle 104 and into wall 157 to form at least one implant 187 in the wall. Preferably a plurality of implants 187 are formed in wall 157, and such a plurality of implants can be arranged in any suitable configuration, such as for example any of the configuration of implants disclosed in U.S. Pat. No. 6,251,063. The injectable material can be deposited into any or all of the layers of wall 157, including between any of such layers. The implant can be of any suitable shape, for example an arcuate implant which extends around a portion or all of the wall as disclosed in U.S. Pat. No. 6,251,064, the entire content of which is incorporated herein by this reference. The implants can serve to augment the wall, bulk the wall, reduce the dispensability of muscle layers 162 and/or 163 of the wall, or serve any other purpose for treating the wall. When the ailment being treated is gastroesophageal reflux disease, the implant can serve to increase the competency of the lower esophageal sphincter 153.

It is appreciated that a suitable injection device, such as injection device 96, can be utilized for forming at least one implant 187 in the wall without the use of probe 22 and be within the scope of the present invention. In this regard, the injection device is introduced into the patient directly, that is not within probe 22, and extended to the vicinity of treatment for creation of the at least one implant.

The ablation of internal surfaces 182 of the wall 157, and the creation of lesion 186 adjacent cavity 181, serves to create a sealed capsule for implant 187 and minimizes or inhibits migration of the implant from cavity 181 into the adjoining tissue. Such a sealed capsule, in combination with introduction of a predetermined amount of implantable material into cavity 181, can advantageously provide an implant 187 of a predetermined volume and thus a procedure for the repeatable creation of appropriately sized implants. It is appreciated that the size and shape of balloon 54, along with the amount of inflation fluid introduced into the balloon 54 during inflation, can be adjusted to vary the size and shape of cavity 181 and thus the size and shape of the resulting implant 187. In this regard, balloon 54 can be spherical, round, semicircular or any other suitable geometric shape.

In another embodiment and procedure of the invention, treatment device 21 does not include an implant-forming apparatus such as injection device 96. In one such embodiment and procedure, no implants are formed or disposed in cavity 181 after the ablation of internal surfaces 182' of the cavity 181 and the creation of lesion 186. Instead, the ablated tissue of the cavity wall and resulting lesion 186 can serve to remodel the tissue structures, reduce the distensibility of the targeted muscle or other tissue of the wall or otherwise treat the tissue and affected area of the mammalian body.

Other embodiments of ablation element 73 can be provided and be within the scope of the present invention. For example, the ablation element 73 can be a bipolar device. FIG. 2 includes a second or return electrode 191, drawn in dashed lines, to illustrate one embodiment of such a bipolar ablation element 73. The return electrode 191 shown in FIG. 2 is substantially similar to first or active electrode 74, and is located on distal extremity 51b of the elongate member 51 within interior 57 of balloon 54 a distance spaced proximally of the active electrodes 74. An additional lead (not shown), which can be substantially similar to lead 75, is electrically coupled to the return electrode 191 and extends through elongate member 51 to an additional connector (not shown), which can be substantially similar to connector 76. Such additional connector is electrically coupled in any suitable manner, for example by a cable (not shown) which can be similar to cable 77, to radio frequency generator and controller 28. When medical device 21 is such a bipolar device, external return electrode 78 is not required.

Figure 13:
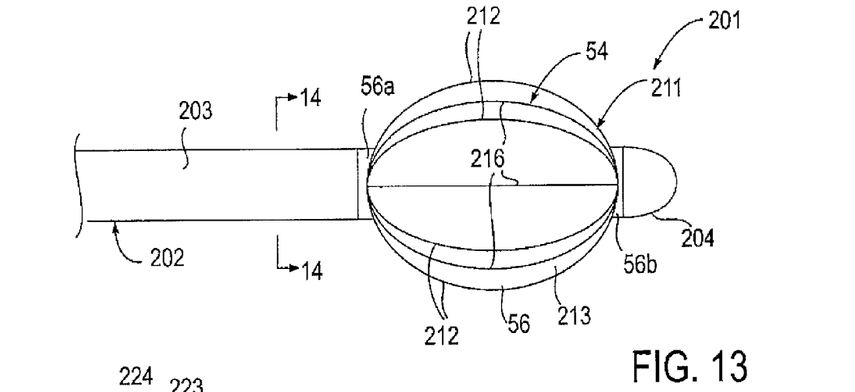
FIG. 13 is a side view, similar to FIG. 2, of another embodiment of the distal extremity of the apparatus for ablating tissue of the present invention.
Figures 14, 15:
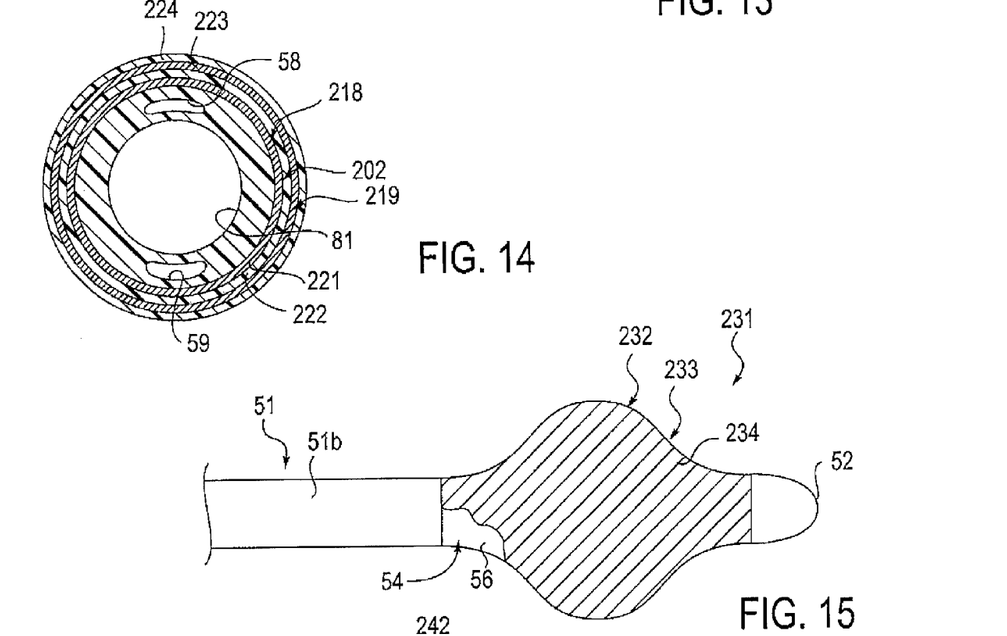
FIG. 14 is a cross-sectional view of the apparatus for ablating tissue of FIG. 13 taken along the line 14-14 of FIG. 13.
FIG. 15 is a side view, similar to FIG. 2 and partially cut away, of a further embodiment of the distal extremity of the apparatus for ablating tissue of the present invention.

Other suitable embodiments of the ablation apparatus of the present invention can be provided. Ablation apparatus 201 illustrated in FIGS. 13 and 14 is substantially similar to ablation apparatus 26 and like reference numerals have been used herein to described like components of ablation apparatus 26 and 201. An elongate member 202, substantially similar to elongate member 51, is included within ablation apparatus 201 and has a proximal extremity (not shown) and a distal extremity 203. The apparatus 201 further includes a rounded end 204 substantially similar to rounded end 56 of the ablation apparatus 26. Ablation apparatus 201 includes a balloon 54 formed from a balloon body 56 having proximal and distal end portions 56a and 56b. An inflation lumen 58 is provided in elongate member 202 for supplying an inflation fluid to balloon 54, and an optional return lumen 59 and passageway 81 can be provided in the elongate member 202 (See FIG. 14). Balloon body 56 is preferably formed without pores 79.

An ablation element 211 is carried by distal extremity 203 of the elongate member 202 and includes at least one active electrode and preferably a plurality of active electrodes 212 carried by external surface 213 of balloon body 56. In the preferred embodiment shown in FIGS. 13 and 14, the plurality of active electrodes 212 include a plurality of longitudinally-extending strips or conductive pathways 212 which each extend from the proximal extremity to the distal extremity of the balloon 54 in circumferentially spaced-apart positions. Ablation element 211 further includes at least one and preferably a plurality of conductive pathways or return electrodes 216 provided on external surface 213 of the balloon 54. The return electrodes are preferably similar in construction to active electrodes 212 and thus extend from the proximal extremity to the distal extremity of the balloon 54 in circumferentially spaced-apart positions. A return electrode 216 is preferably spaced between each adjacent pair of active electrodes 212, with the spacing between each adjacent active electrode and return electrode being approximately equal. The active and return electrodes 212 and 216 can be formed in any suitable manner, for example such electrodes can each be formed from a wire or a machined shape, or from a material such as a conductive ink, metallic particles, conductive polymers or a stamp formed on the outer surface 213 of the balloon body 56.

At least one first or active lead 218 extends through elongate member 202 for providing electrically energy, preferably in the form of radio frequency energy, to the active electrodes 212, and at least one second or return lead 219 extends through the elongate member 202 for receiving energy from the return electrodes 216. Each of the leads 218 and 219 is coupled at its distal end to their respective electrode or electrodes and at its proximal end to a connector, for example a connector similar to connector 76, for permitting electrical communication between the active and return electrodes and radio frequency generator and controller 28. Active and return leads 218 and 219 can be formed in any suitable manner. For example, one of the leads, such as active lead 218, can be in the form of a first coating 221 which is annular in cross section, as shown in FIG. 14, and extends from the proximal extremity to the distal extremity 203 of elongate member 202. A nonconductive or insulative coating 222 is disposed around substantially the entire length of the first conductive coating 221. The second lead, such as return lead 219, can be formed from a similar second conductive coating 223 disposed around first nonconductive coating 222 from the proximal extremity to the distal extremity 203 of the elongate member 202. A second nonconductive or insulative coating 224 extends around substantially the entire length of the second conductive coating 223. First and second conductive coatings 221 and 223 are made from any suitable material or materials such as a metal or a polymer and preferably gold, silver, platinum, iron oxide particles and other conductive elements and more preferably gold or a conductive polymer, and can be formed in any suitable manner such as dip coating, spraying, plating or vapor deposition. First and second insulative coatings 222 and 224 can be made from any suitable material or materials such as a thermoplastic or a thermoplastic elastomer such as polytetrafluoroethylene, polyurethane, silicone and other non-conductive elements and preferably polyurethane, and can be formed in any suitable manner such as blow molding, injection molding, shrink wrapping or tubing, dip coating, spraying and extrusion.

Ablation apparatus 201 is operated with probe 22 in substantially the same manner as discussed above with respect to ablation apparatus 26 to form an implant in wall 157 that is less susceptible to migration. In this regard, a cavity 181 is formed in the wall 157 by dissecting balloon 54. The one or more active electrodes 212 of the ablation apparatus are energized with radio frequency energy supplied by generator and controller 28 to create a lesion 186 around the cavity. An implantable material is introduced into the cavity 181 with injection device 96 to form an implant in wall 157.

Bipolar ablation apparatus 201 can be simplified to provide a monopolar ablation apparatus for use with an external indifferent or return electrode such as return electrode 78 discussed above. Such a monopolar ablation apparatus does not include return electrodes 216 on balloon 54 and, instead, merely includes a plurality of circumferentially spaced-apart active electrodes 212 on external surface 213 of the balloon body 56. Similarly, the return lead 219 formed from second conductive coating 223, and the related second nonconductive coating 224, are not required in such a monopolar ablation apparatus. It is appreciated, however, that ablation apparatus 201 can also be operated in a monopolar mode by supplying radio frequency energy to both active and return leads 118 and 119 so that both sets of electrodes 212 and 216 serve as active electrodes.

The bipolar apparatus of the invention, for example bipolar ablation element 73 with return electrode 191 and bipolar apparatus 201, are advantageous because they typically can eliminate the need for a grounding pad or other return electrode external of the body. Such elimination can reduce the cost and steps of a procedure utilizing such an apparatus, thus providing a simplified procedure. In addition, locating a return or inactive electrode in close proximity to the active electrode, such as in a bipolar device, can serve to better concentrate radio frequency energy in the targeted tissue and thus increase the efficacy of a procedure employing such bipolar or other active and inactive electrodes in such close proximity to each other in comparison to a related monopolar procedure.

A further embodiment of an ablation apparatus of the present inventions is shown in FIG. 15. Ablation apparatus 231 therein is substantially similar to ablation apparatus 26 and like reference numerals have been used to describe like components of ablation apparatus 26 and 231. An elongate member 51, having a balloon 54 at its distal extremity, is included within ablation apparatus 231. An inflation lumen 58 (not shown) extends through the elongate member 51 and optional return lumen 29 and passageway 81 (not shown) can also extend through the elongate member 51. Balloon body 56 is preferably formed without pores 79.

An ablation element 232 is included within the ablation apparatus 231 and preferably includes a single electrode 233 formed on at least a portion of, and preferably the entire external surface of, balloon body 56 (see FIG. 15). Electrode 233 is formed in any suitable manner and is preferably formed from a conductive coating 234 made from any suitable material or materials such as a metal or a polymer and preferably gold, silver, platinum, iron oxide particles and other conductive elements and more preferably gold or a conductive polymer, and can be formed in any suitable manner such as dip coating, spraying, plating or vapor deposition. Active electrode 233 is electrically coupled to radio frequency generator and controller 28 by any suitable means such as a lead 75 (not shown), or alternatively lead 218 of ablation apparatus 201 (not shown), extending through the elongate member 51 of ablation apparatus 231.

Figure 16:
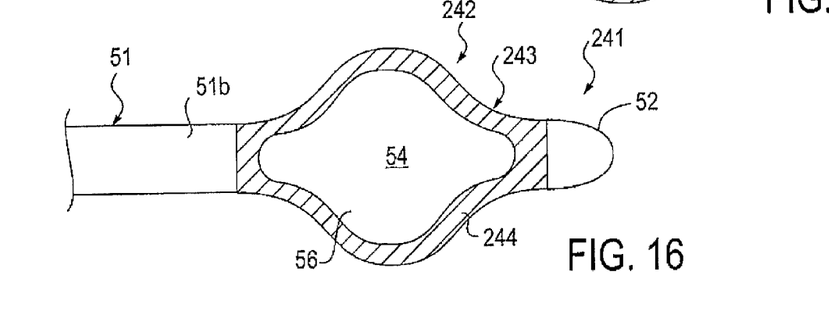
FIG. 16 is a side view, similar to FIG. 2, of yet another embodiment of the distal extremity of the apparatus for ablating tissue of the present invention.

An ablation apparatus 241 having similarities to ablation apparatus 231 is shown in FIG. 16, and like reference numerals have been used to describe like components of ablation apparatus 231 and 241. Balloon body 56 of the ablation apparatus 241 does not include pores 79. An ablation element 242 having a single active electrode 243 is included within ablation apparatus 241. Electrode 243 is formed from a conductive coating 244 which is substantially similar to the conductive coating 234 of ablation apparatus 231 but extends over only a portion of balloon body 56. Specifically, conductive coating 244 extends around the circumference of the balloon 54.

Ablation apparatus 231 and 241 can be operated with probe 22, preferably in a monopolar operation, in substantially the same manner as discussed above with respect to ablation apparatus 26 but without the weeping of a conductive fluid from the outer surface of balloon body 56. After a cavity 181 is formed in the wall 157 by dissecting balloon 56, the conductive coating of such apparatus is energized with radio frequency energy to ablate internal surfaces 182 forming such cavity 181.

In another procedure of the invention, an implant formed by one or more conductive beads or other bodies is created in cavity 181 formed by wall 157. The conductive beads or bodies can be introduced into wall 157 by means of a tubular needle assembly or any other suitable means, and utilized to create cavity 181 or introduced into the cavity after creation of the cavity. Radio frequency energy can be supplied to such conductive beads or bodies, for example by a conductive lead or by saline or another conductive liquid in each case coupled directly or indirectly to such conductive beads or bodies, to ablate the wall 157 around cavity 181 and form a lesion 186 in the wall. Such conductive beads or bodies can be of any suitable type and formed from any suitable material such as metal. Where biocompatible beads or bodies are so utilized, they can remain in cavity 181 and serve as an implant for treating the tissue of the wall in the manner discussed above. Alternatively, the beads or bodies can be removed from cavity 181 in any suitable manner after tissue ablation, for example by incising the wall to access the cavity 181 or by introducing a tubular removal member into the cavity, and lesion 186 can serve to treat the tissue of the wall in the manner discussed above.

As can be seen from the foregoing, a method and apparatus have been provided for forming implants of a predetermined size at a desired location in the tissue of a mammalian body. The method and apparatus can inhibit migration of the implants within the tissue.

What is claimed is:

1. A method for treating a mammalian body having tissue comprising:
creating, via blunt dissection, a new cavity in the tissue formed by an internal surface of the tissue by inserting a distal extremity of a flexible elongate member into the tissue;
ablating, via an ablation element, the internal surface; and
introducing, via the flexible elongate member, an implant-forming material into the cavity to create an implant in the tissue whereby the ablation of the internal surface inhibits migration of the implant from the cavity into adjoining tissue.

2. The method of claim 1, wherein the creating step includes the step of dissecting the tissue via an incising element by moving the incising element within the distal extremity of the flexible elongate member between an extended position in which the incising element projects distally from a distal extremity of the flexible elongate member for introducing a rounded distal end of the flexible elongate member and an expandable-collapsible body to a target position and a retracted position permitting use of the rounded distal end for blunt dissection.

3. The method of claim 2, wherein the ablating step includes utilizing the expandable-collapsible body to ablate the tissue.

4. The method of claim 3, wherein the ablating step includes energizing conductive pathways on a surface of the expandable-collapsible body.

5. The method of claim 3, wherein the ablating step includes energizing a conductive coating on a surface of the expandable-collapsible body.

6. The method of claim 2, wherein the expandable-collapsible body is inflated with a conductive material and the ablating step includes weeping the conductive material from the expandable-collapsible body.

7. The method of claim 6, wherein the ablating step includes energizing an electrode within the expandable-collapsible body to couple radio frequency energy to the conductive material.

8. The method of claim 2, wherein the creating step includes introducing the incising element into tissue of a wall of the body, forming a natural body cavity in the body.

9. The method of claim 8, wherein the creating step includes introducing the distal extremity into a natural body opening to access the natural body cavity.

10. The method of claim 9, wherein the creating step includes providing a lumen within the flexible elongate member which extends to and opens at the distal extremity of the flexible elongate member and sliding the incising element through the lumen to the distal extremity of the flexible elongate member.

* * * * *